United States Patent [19]

Perry et al.

[11] 3,955,119
[45] May 4, 1976

[54] APPARATUS FOR PREDICTING INCIPIENT FAILURE OF AN X-RAY GENERATOR TUBE

[75] Inventors: John T. Perry, Salt Lake City, Utah; James A. Grichnik, Park Ridge; Joel J. Schmutzer, Oak Park, both of Ill.

[73] Assignee: Varian Associates, Palo Alto, Calif.

[22] Filed: Oct. 11, 1974

[21] Appl. No.: 514,157

Related U.S. Application Data

[63] Continuation of Ser. No. 327,259, Jan. 29, 1973, abandoned.

[52] U.S. Cl. .............................. 315/133; 250/416; 315/135; 315/136
[51] Int. Cl.² .......................................... H05G 1/30
[58] Field of Search ........... 315/129, 133, 135, 136; 250/401, 402, 406, 413, 414, 416

[56] References Cited
UNITED STATES PATENTS

| | | | |
|---|---|---|---|
| 2,172,581 | 9/1939 | Horsley | 315/129 X |
| 3,062,960 | 11/1962 | Laser | 250/406 |
| 3,244,884 | 4/1966 | McLaughlin | 250/406 |
| 3,518,434 | 6/1970 | Lombardo | 250/406 |
| 3,564,254 | 2/1971 | Siedband et al. | 250/414 X |
| 3,634,871 | 1/1972 | Siedband et al. | 250/416 X |
| 3,746,862 | 7/1973 | Lombardo | 250/416 X |

*Primary Examiner*—James B. Mullins
*Attorney, Agent, or Firm*—Stanley Z. Cole; John J. Morrissey; Richard B. Nelson

[57] ABSTRACT

Failure inducive operating conditions of an X-ray generator tube are sensed. Some of the sensed operating conditions are events such as hot overload of the target and thermal shock of the target, while other sensed operating conditions include hot target bearing use and thermionic cathode filament heater use. Certain of the sensed operating conditions are integrated, with the integrated output being compared against a predetermined standard to yield a prediction of remaining operating life. Other sensed conditions, if present, are indicative of incipient failure without integration. The integrated signals are stored in electrochemical cells and read out periodically for a prediction of incipient tube failure.

22 Claims, 6 Drawing Figures

APPARATUS FOR PREDICTING INCIPIENT FAILURE OF AN X-RAY GENERATOR TUBE

This is a continuation of Ser. No. 327,259, filed Jan. 29, 1973, now abandoned.

BACKGROUND OF THE INVENTION

The present invention relates in general to method and apparatus for predicting incipient failure of an X-ray generator tube and more particularly to an improved monitoring apparatus for monitoring several of the operating conditions of the X-ray tube to yield an indication of incipient failure thereof.

DESCRIPTION OF THE PRIOR ART

Heretofore, certain operating parameters of an X-ray generator tube have been monitored to yield an indication of a malfunction of the tube or an indication of operating hours on the tube. In one prior example, the back electromotive force (e.m.f.) on the stator winding of the target rotation motor of the X-ray tube is monitored. An excessive back e.m.f. indicates bearing failure or failure of the target to reach operating speed.

It is also known from the prior art that the anode voltage applied to the X-ray generator tube can be monitored and integrated to yield an output proportional to the total exposure time on the tube.

The problem with these prior tube monitoring devices is that they do not provide a satisfactory overall prediction of incipient failure of an X-ray generator tube. In the case of the prior stator back e.m.f. method, this indicates a failure of the tube but does not provide a prediction of an incipient failure. In the case of the exposure time monitoring method, the monitoring circuit provides an output proportional of the operating time on the tube but does not provide a prediction of the remaining life of the tube.

There is a need for a monitoring circuit for monitoring the operating conditions of an X-ray generator tube in order to accurately predict an incipient failure of the X-ray tube. Such tubes are often utilized in relatively complicated surgical procedures and a failure of the X-ray tube during the operating procedure could jeopardize the success of the operation and/or cause the operating procedure to be repeated.

SUMMARY OF THE PRESENT INVENTION

The principal object of the present invention is the provision of means for predicting incipient failure of an X-ray generator tube.

In one feature of the present invention, a failure inducive operating condition of the X-ray generator tube is sensed to derive a failure mode output. This output is integrated, and the integrated output is compared to a predetermined standard for indicating incipient failure when the integrated failure mode output exceeds a predetermined value.

In another feature of the present invention, excessive vibration of the X-ray tube is detected as a consequence of target rotation to derive an output indicative of incipient failure of the bearing support for the rotatable X-ray target.

In another feature of the present invention, an output is obtained indicative of the heat units stored in the X-ray target. This output is compared with a predetermined reference to derive an overload signal whenever the heat units stored in the target exceed a predetermined value.

In another feature of the present invention, beam power delivered to the X-ray target is monitored to derive an overload signal whenever the beam power absorbed in the target exceeds a predetermined reference value for a predetermined time period.

In another feature of the present invention, cathode heater filament usage is monitored to derive an output indicative of operation of the X-ray tube at an output level above the fluoroscopic level, such output being integrated and compared with a reference to yield an indication of incipient failure whenever usage of the X-ray tube at higher than fluoroscopic level exceeds a predetermined value.

In another feature of the present invention, the coasting time of the rotatable target is monitored to derive a failure mode output whenever the coasting time of the target falls below a predetermined value.

In another feature of the present invention, a failure mode output signal is integrated in an electrochemical cell, such cell being periodically read out to derive an output proportional to the remaining useful life of the X-ray generator for that particular mode of failure.

Other features and advantages of the present invention will become apparent upon a perusal of the following specification taken in connection with the accompanying drawings wherein:

DESCRIPTION OF THE PREFERRED EMBODIMENTS

Figure 1:
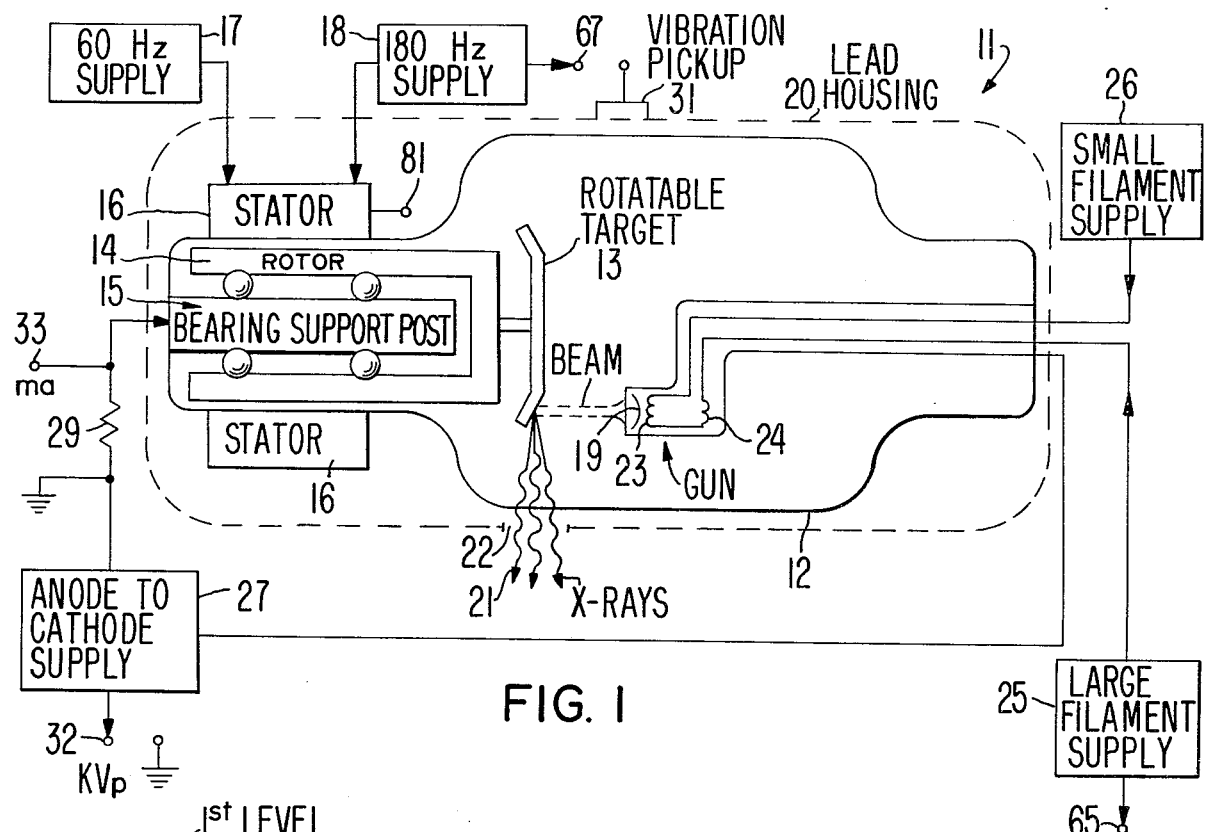
FIG. 1 is a schematic line diagram, partly in block diagram form, of an X-ray generator tube of the type to be monitored by the apparatus of the present invention.

Referring now to FIG. 1 there is shown an X-ray generator tube 11 of the type to be monitored by the circuitry of the present invention. More particularly, the X-ray generator tube 11 includes an elongated evacuated envelope 12 as of glass having a rotatable X-ray target 13, as of tungsten, carried from a rotor 14 within the envelope 12 via a bearing assembly 15. A stator winding 16 is disposed externally of the envelope 12 around the rotor 14. The stator winding 16 is selectively energized with power from a pair of power supplies 17 and 18 supplying drive power at 60 hertz and 180 hertz, respectively, to produce rotation of the rotor 14 and target 13 at rotation frequencies of 3500 r.p.m. and 10,000 r.p.m., respectively, depending upon which of the power supplies 17 and 18 is selectively energized.

A thermionic cathode emitter 19 is disposed within the envelope 12 in axial alignment with the periphery of the rotatable target 13 for directing a stream of electrons of high energy onto the peripheral edge of the target 13. Electron bombardment of the target generates a lobe of X-rays 21 passing through the envelope 12 and through an aperture 22 in a lead housing 20 surrounding the envelope 12. The lead housing 20 shields the surrounds from unwanted X-ray radiation.

The thermionic cathode emitter 19 is heated to thermionic emission temperature via either one of two filamentary heaters 23 and 24 disposed at the backside of the thermionic cathode emitter 19. Filamentary heater 23 is substantially larger than heater 24 and takes a substantially higher power flow therethrough for heating the cathode 19 to a substantially higher operating temperature such that the beam current incident upon the target anode 13 is substantially above the level of radiation employed for fluoroscopic usage. The second filamentary cathode heater 24 is substantially smaller than the first and designed to consume substantially less power for heating the cathode emitter 19 to a lower temperature such that the beam current at the lower temperature of operation is such as to deliver a substantially lower power to the anode target 13. Filament power supply 25 supplies filament power to the large filament 23, whereas filament supply 26 supplies a lesser power to the smaller cathode heater 24.

An anode-to-cathode power supply 27 is connected between the cathode emitter 19 and the target anode 13 via the intermediary of a stationary bearing support post and ball bearings of its bearing assembly 15. A resistor 29 is connected in series with the anode-to-cathode supply 27 to derive a voltage output signal thereacross which is proportional to the milliamps of beam current flowing through the tube. A piezo-electric vibration pickup, such as a phonographic needle pickup cartridge 31 is affixed to the housing 20 for picking up the vibration of the X-ray tube and housing as caused by rotation of the target 13.

Figure 2:
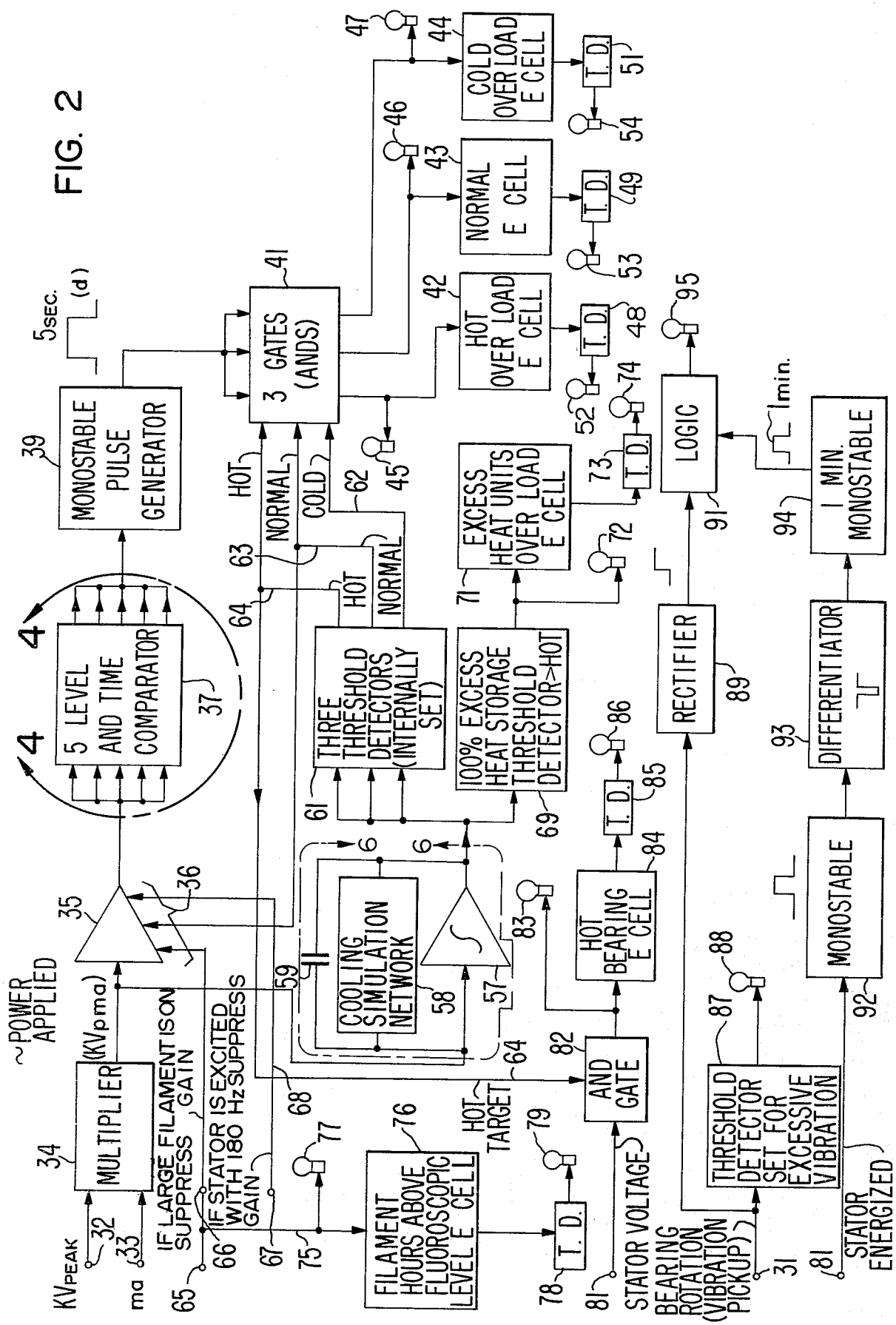
FIG. 2 is a schematic block diagram of an X-ray generator tube monitoring circuit of the present invention.

Referring now to FIG. 2 there is shown the electrical circuitry for monitoring failure inducive operating conditions of the X-ray generator tube 11 and for predicting incipient failure of the tube 11. A number of the failure inducive operating conditions that are monitored by the circuitry of FIG. 2 involve overloading the heat capacity of the rotatable anode target 13. There are a number of ways that the heat capacity of the target can be overloaded. First the target has a certain maximum permissible total heat storage capacity. If this is exceeded then the operating life of the tube is reduced. Secondly, the target may be heat shocked, that is, the instantaneous power consumed in the X-ray target may exceed a normal stress level. This is further complicated since the normal stress level is also a function of the temperature of the target or present heat storage condition of the target. More particularly, if the target is hotter or colder than normal the amount of heat units that can be absorbed by the target in a given period of time, without producing undue stress on the target, will be reduced.

Accordingly, the monitoring circuit of FIG. 2 simulates the heat storage condition of the target 13 by multiplying, in multiplier 34, the peak voltage output of the cathode-to-anode power supply $KV_p$, derived from terminal 32 of the supply 27, with the milliampere anode current signal ma, derived from terminal 33, to derive an output proportional to $KV_p \cdot ma$. This signal is approximately proportional to the beam power input to the target 13. The output of the multiplier 34 is fed to the input of a variable gain amplifier 35 having a voltage gain of unity or less depending upon the degree of gain suppression supplied to gain control inputs 36. The output of the amplifier 35 is fed to a five level and time comparator circuit 37, one channel of which is shown in greater detail in FIG. 4.

Figure 3:
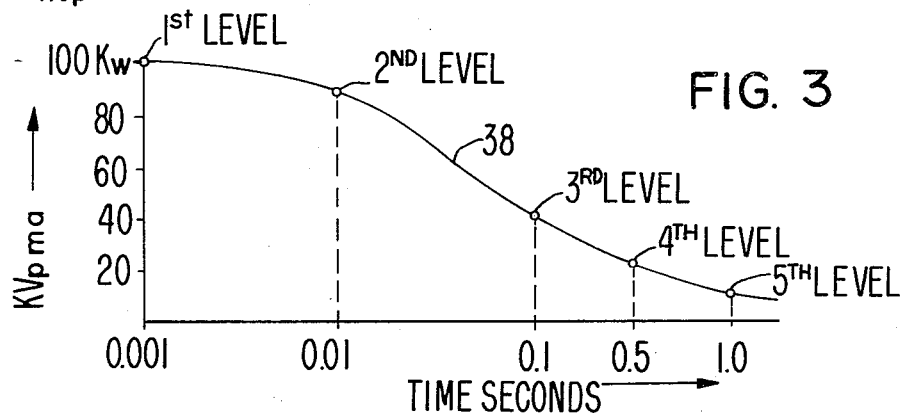
FIG. 3 is a plot of maximum rated input beam power to the X-ray target as a function of time for a typical X-ray generator tube.

Referring now to FIG. 3 there is shown a plot of input beam power to the target 13 in Kilowatts versus time depicting, at curve 38, the maximum rated input power to the target without derating the operating life of the tube. The five level and time comparator circuit 37 includes five separate channels of the type shown in FIG. 4 for monitoring the input power versus time characteristic applied to the X-ray target 13. The five separate levels correspond to five separate time intervals, as of 0.001 seconds, 0.01 seconds, 0.1 seconds, 0.5 seconds and 1.0 seconds. The permissible input power to the target 13 for those various times are indicated as the first level, second level, third level, fourth level and fifth level points on curve 38. If any of the input power levels are exceeded for the respective time indicated on the abscissa, then a failure mode output signal is derived from circuit 37 and fed to a monostable pulse generator 39 (FIG. 2) for generating a pulse of a predetermined current amplitude and duration, as of 5 seconds duration, which is thence fed through a gating circuit 41 to a respective HOT, NORMAL, or COLD overload electrochemical integrating cell 42-44, respectively. Indicator lights 45, 46 and 47 are connected to the respective outputs of the gates 41 for indicating an instantaneous overload or failure mode output event. Threshold detectors 48, 49 and 51 are connected across the respective electrochemical cells 42-44 for monitoring a completely discharged condition or deplated condition of the respective cells 42-44.

Each of the electrochemical cells 42-44 has two electrodes immersed in an electrolyte; one is initially plated (charged) to a value corresponding to an expected lifetime of such overload events and the other is initially deplated. In this manner, as each of the overload events is charged into the respective overload cell 42-44 it removes a certain fraction of the plating from the initially plated electrode of the cell and deposits this plating on the other electrode. Accordingly, when the predetermined total number of such overload events, represented by the plating in each of the individual cells, is fed into each of the individual cells, the plated electrode thereof will be completely deplated and the respective cell will be thereby completely discharged. Upon complete deplating of the initially plated electrode of the respective cell 42-44, the impedance of the cell increases by a factor of at least 100. Thus, the voltage drop across the cell substantially increases. It is this increase in voltage drop across the cell that is monitored by the respective threshold detector 48-51 to yield an output determinative of an incipient failure of the X-ray generator tube. This incipient failure output is then fed to a respective indicator lamp 52-54 for indicating an incipient failure. A suitable electrochemical integrating cell 42-44 comprises an electrochemical integrator or counter, such as a Plessey series 560 cell available from Plessey Electroproducts of Los Angeles, California.

A representative channel of the five level and time comparator circuit 37 is shown in greater detail in FIG.

4. More particularly, the input derived from the output of amplifier 35 corresponds to the input power to the target modified by the gain of the amplifier 35, in a manner more fully described below. This input is thence fed to the input of a threshold detector 55 having a predetermined internal reference value determinative of one of the aforecited five reference levels indicated in FIG. 3. If the input voltage exceeds the respective reference level of the threshold detector 55, an output pulse is generated as shown by waveform a of FIG. 4. The output pulse will have a duration dependent upon the length of time that the input power exceeds the predetermined reference level. The output of the threshold detector is fed to the input of a monostable pulse generator 56 set for a predetermined time corresponding to the respective time as set forth on the abscissa of FIG. 3, namely the time corresponding to the intersection of the time coordinate with the power level coordinate of curve 38.

Figure 4:
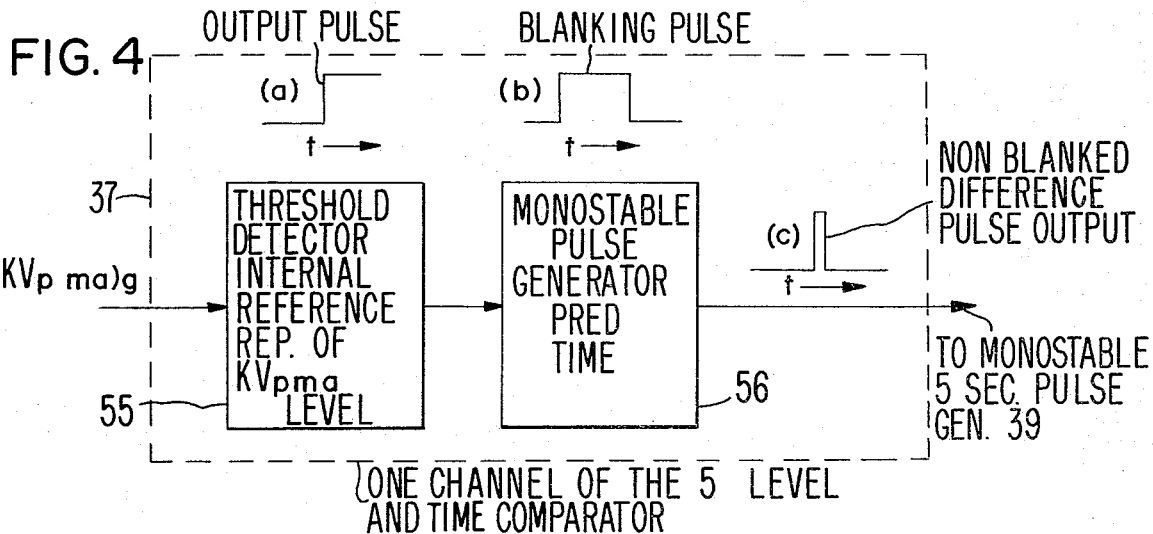
FIG. 4 is a schematic block diagram for one channel of the five level and time comparator circuit portion of FIG. 2 delineated by line 4—4.

The monostable pulse generator 56 generates a blanking pulse of a predetermined duration corresponding to the particular abscissa coordinate. Blanking pulse, waveform b, serves to blank out the output pulse of the threshold detector for the duration of the blanking pulse. If the output of the threshold detector 55 is of a longer duration than the blanking pulse, a non-blanked difference output pulse is derived at the output of the monostable pulse generator 56. This non-blank difference pulse is shown by waveform c and is representative of the occurrence of a failure mode event which is thence fed to the monostable pulse generator 39 for generating the 5 second event pulse as shown by waveform d (FIG. 2). The five level and time comparator circuit 37 includes five separate channels of the type as shown in FIG. 4 and each channel is set for a different reference power level and for a respectively different time base, as shown in FIG. 3.

Referring again to FIG. 2, a second output signal of the multiplier 34, which is a measure of the power that is dissipated as heat in the target 13, is fed to the input of an integrating amplifier 57, which together with a capacitor 59 comprises a leaky integrator that accumulates the power dissipation signal as a function of time such that the output of the integrating amplifier 57 approximates the heat storage of the X-ray target 13. More particularly, the peak power output signal derived from the output of multiplier 34 is integrated by integrating amplifier 57. The output of integrating amplifier 57 is moderated or dissipated at a rate determined by the heat dissipation simulation network 58 which discharges the capacitor 59 at a rate which approximates the cooling effect of the target 13.

Figure 6:
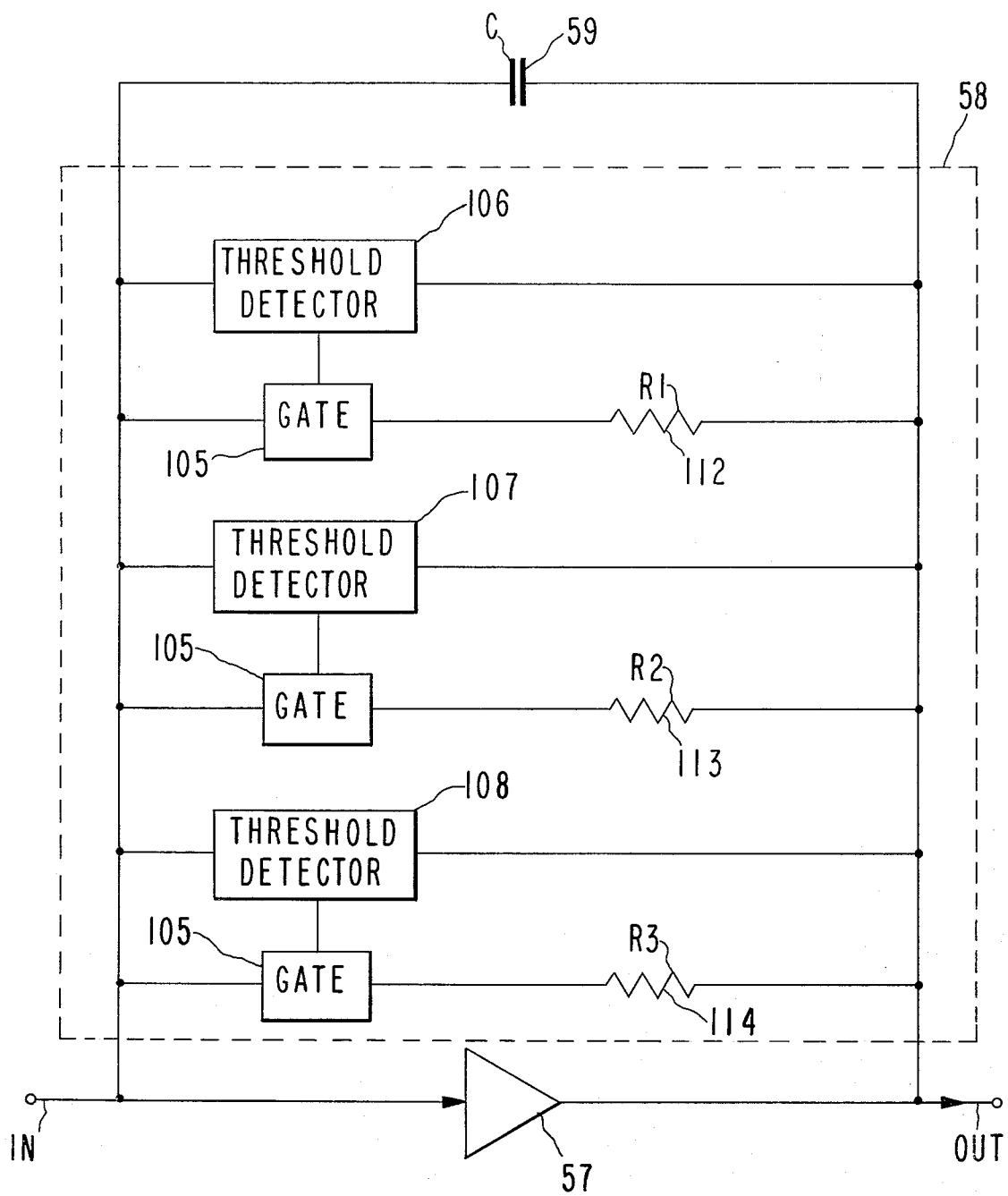
FIG. 6 is a schematic circuit diagram, partly in block form, of the target heat simulation circuit of FIG. 2.

Heat dissipation network 58 includes 3 to 5 parallel circuit branches each connected in parallel with capacitor 59. A suitable heat dissipation simulation network is shown in detail in FIG. 6. Each circuit branch includes a series connection of a different value of resistance (e.g., 112, 113 or 114) and a gate 105 controlled by a threshold detector (e.g., 106, 107 or 108) for gating a respective resistor in circuit parallel with the capacitor 59. The respective gated resistors are of respective values of resistance which are inversely related to the heat storage output of integrator 57 such that for a cold or low value of heat storage in the target, as sensed by the low value threshold detector, a relatively high value of resistance is gated into parallel with capacitor 59 to provide a relatively long time constant, as of 1 hour, to simulate the low cooling rate for a cold target, whereas a low value of resistance is gated into parallel with capacitor 59 for a hot target to simulate a relatively high cooling rate of a hot target.

The output of the leaky integrator 57 is fed to the input of three separate threshold detectors 61. Each threshold detector has internal threshold references set for a different voltage level range corresponding to respectively different ranges of heat storage in the X-ray target 13. More particularly, the first threshold detector is set for detecting heat storage units in the target within the range from zero to 0.05. If the input signal falls within that range, an output is derived on lead 62 indicative of a cold condition of the target 13. This cold signal is fed to the cold input of one of the three AND gates 41 for gating the output of the pulse generator 39 to the cold overload cell 44. If the input signal to the second threshold detector is within the range of 0.05 to 0.5 heat units, an output corresponding to the NORMAL operating condition of the target 13 is obtained on lead 63, which is fed to the NORMAL input of one of the three gates 41 for gating the output of the pulse generator 39 to the NORMAL overload cell 43. Likewise, if the output of the leaky integrator 57 is greater than 0.5 heat units, the third threshold detector channel of detector 61 produces an output on lead 64 which is fed to one of the three gates 41 for gating the output of the pulse generator 39 to the HOT overload integration cell 42.

Since the acceptable number of instantaneous heat units that may be absorbed in the X-ray target 13 without producing thermal shock depends upon the number of heat units already stored in the target, an output is derived from the NORMAL output lead 63 of threshold detector 61 and fed to one of the gain control inputs 36 of the amplifier 35 for reducing the gain of the amplifier 35 to 70% of its normal gain. This allows the instantaneous power applied to the target 13 to be greater by 30% than that applied to a HOT or COLD target 13 without triggering one of the respective threshold detectors in the five level time comparator circuit 37. Such a reduction in the gain is not obtained when the target is operating hot or cold as determined by the output of the three threshold detectors 61.

The gain of amplifier 35 is likewise suppressed to a preset value in the range of 30-70% dependent directly upon beam spot size if the large filament heater is energized, such signal being obtained from terminal 65 of the large filament supply via line 66. Similarly, the gain of amplifier 35 is reduced to approximately 50% of its normal value if the target 13 is rotated at the higher angular velocity as determined by energization of the stator from the 180 hertz supply as derived from terminal 67 via line 68. The gain control inputs 36 are arranged such that if any one or more of the gain control inputs 36 is energized (TRUE) the gain of amplifier 35 is reduced from its normal value.

A second output of the leaky integrator 57 is fed to an excess heat storage threshold detector 69 set for a predetermined threshold value representative of a maximum permissable heat storage state of the target 13. If the predetermined reference level of threshold detector 69 is exceeded, its "TRUE" output is indicative of excessive heat storage or overloading of the target 13. The "TRUE" output is a predetermined current value that persists for as long as heat storage of the target 13 is excessive. This overload output signal is fed to an excess heat unit electrochemical integrating cell 71 of the type previously described with regard to cells

42–44. A TRUE output is also derived from threshold detector 69 and fed to an indicator lamp 72 to give an instantaneous indication of an overload state of the target 13. The output of the integrator cell 71 is monitored by a threshold detector 73 for detecting complete discharge or deplating of the initially plated electrode of the integrator cell 71. Upon detection of the discharge of cell 71, the output of the threshold detector 73 lights an indicator lamp 74 indicating an incipient failure of the X-ray generator tube 11.

A signal determinative of large heater filament energization is derived from terminal 65 via lead 76 and fed to the input of a "filament hours above fluoroscopic level" electrochemical integration cell 76 for deplating the plated electrode thereof. The initially plated electrode is initially plated to a value indicative of the expected operating life of the X-ray tube at a level above fluoroscopic level. An indicator lamp 77 is connected to terminal 65 for indicating that the tube is operating at an output level above the fluoroscopic level. A threshold detector 78 monitors the state of discharge or deplating of cell 76 for delivering an incipient failure mode output to an indicator lamp 79 when the cell 76 is deplated, thereby yielding an indication of an incipient failure of the X-ray generator tube 11.

The expected operating life of the X-ray tube is also dependent upon the total duration of target bearing support use during time intervals when the target 13 is in a hot condition. Accordingly, an output is derived from the stator winding at 91 indicative that the stator is energized and thus that the target is rotating. This rotation signal is fed to one input of an AND gate 82 for ANDING with a HOT signal output from lead 64 of the third one of the three threshold detectors 61, such HOT output being indicative of a hot condition of the target 13. The TRUE output of the AND gate 82 is fed to an indicator lamp 83 indicative that the tube is being operated in a possible failure mode. A second constant current TRUE output of the AND gate 82 is fed to a hot bearing integrator electrochemical cell 84, of the type previously described with regard to element 42-44, for integrating the hot bearing usage. The hot bearing integrator cell 84 is monitored by a threshold detector 85 which senses when the cell is deplated from the expected operating life condition for hot bearing mode usage. When the threshold 85 senses a deplating of cell 84, it lights an indicator lamp 86, thereby indicating an incipient failure of the X-ray tube 11.

Excessive vibration of the tube 11 is an indication of bearing failure. Therefore the output of the vibration pickup 31 is fed to the input of a threshold detector 87 which has an internal reference set for a predetermined excessive state of vibration. Thus when the vibration of the X-ray tube, as detected by pickup 31, exceeds a predetermined value, an indicating lamp 88 is lighted, thereby indicating an incipient failure of the X-ray tube.

Also, if the rotating target fails to coast for a predetermined time, such as for 1 minute after deenergization of the stator, this is an indication that the bearings for the rotating target are defective and an indication of incipient failure of the tube 11. Therefore, an output of the vibration pickup 31 is fed to a rectifier 89 for rectification and thence to the input of a logic circuit 91 for comparison with a second signal derived from the stator energization terminal 81. More particularly, the output of the stator coil is fed to a monostable pulse generator 92 which generates a pulse of a duration determined by the duration of the energization of the stator winding. Upon termination of the energization of the stator winding, the monostable pulse generator output 92 drops to zero. The output of the monostable pulse gennerator 92 is fed to a differentiator which detects the trailing edge of the output pulse of the monostable pulse generator 92. The trailing edge output of the differentiator 93 is fed to the input of a monostable pulse generator 94 which generates a pulse of a predetermined duration, as of 1 minute. The 1 minute pulse is then fed to the second input of the logic circuit 91 for comparison with the output of the rectifier 89. The logic circuit 91 includes a comparator network for comparing the two inputs to generate a failure mode output signal if the output of the rectifier 89 is not present during the entire duration of the one minute output pulse of the monostable pulse generator circuit 94. The failure mode output of logic circuit 91 is fed to a latching indicator lamp 95 for indicating an incipient failure of the target bearings and thus of the X-ray tube 11.

Figure 5:
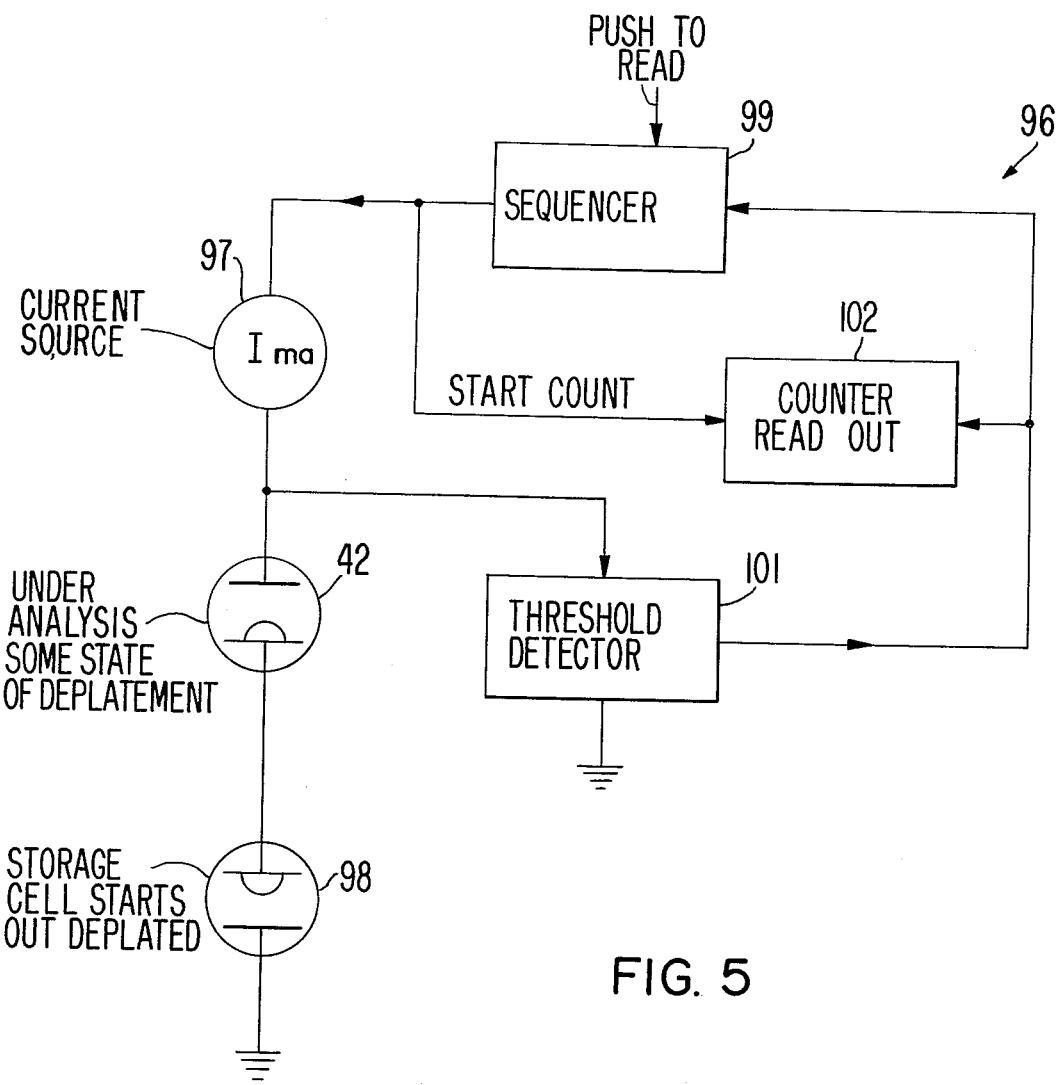
FIG. 5 is a schematic circuit diagram, partly in block diagram form, of a read out circuit for reading out the integrated failure mode output signal in the electrochemical cells of FIG. 2.

Referring now to FIG. 5 there is shown a read out circuit 96 for reading out the state of deplatement of any one of the integrator cells 42–44, 71, 76 or 84. The cell to be read out, such as cell 42, is connected in series between a constant current source 97 and a second electrochemical integrator cell 98 identical to cell 42 but initially in a condition of being completely deplated. Since cell 42 starts out with the recording electrode completely plated, the integrated output of cell 42 corresponds to the state of deplatement of the plated electrode. Accordingly, a sequencer 99 includes a push-to-read switch which is depressed by the operator. The sequencer 99 starts deplatement of the cell 42 and a corresponding platement of cell 98 since the same current flows from current source 97 through the cell 42 to be read out and the storage cell 98. A threshold detector 101 is connected across cells 42 and 98 to detect when the cell 42 has reached a condition of complete deplatement. Meanwhile, energization of the push-to-read switch in the sequencer 99 applied an output to a counter 102 which started counting such that the output of counter 102 indicates the expected remaining life of the quantity being analyzed.

Threshold detector 101 detects complete deplatement of cell 42 and an output is produced which gates off the sequencer 99 and counter 102 such that the count is stopped at the value corresponding to the remaining life of the quantity under analysis. After the cell 42 has thus been read out, the positions of cells 98 and 42 are reversed such that the storage cell 98, which has thus been plated, is deplated back into cell 42 to return cell 42 to its previous state of platement. Cell 42 is then plugged back into the circuit of FIG. 2.

Actually for convenience, all the integrator cells 42-44, 71, 76 and 84 are mounted in a single plug in unit. The respective storage read out cells 98 are mounted within the reader 96. The read out circuit 96 includes a selector switch for selecting a desired one of the integrator cells to be read out. After read out the read out cell is recharged from its storage mate.

What is claimed is:

1. An apparatus for predicting failure of an X-ray generator tube, comprising:
    means for monitoring a failure inducive operating condition of said tube,
    means for deriving an output signal indicative of the value of said failure inducive operating condition, means for generating a failure mode output when said output signal exceeds a predetermined value, means for integrating successive failure mode outputs, and means for indicating a value of said integrated failure mode outputs.

2. The apparatus of claim 1 wherein said means for indicating a value of said integrated failure mode comprises means for indicating incipient failure when said integrated failure mode outputs pass a value predetermined to indicate incipient failure.

3. The apparatus of claim 1 wherein said failure inducive operating condition is the heat storage in the target in said tube.

4. The apparatus of claim 1 wherein said failure inducive operating condition is the energization of the cathode heater in said tube.

5. The apparatus of claim 1 wherein said integrating means is an electrochemical cell having first and second electrodes, said failure mode outputs being applied as current charged into said cell, said integrating being by removal of plating from said first electrode and deposition of said plating on said second electrode.

6. The apparatus of claim 5 including reading means for reading out the value of said integrated failure mode outputs, said reading means comprising means for completely deplating one of said electrodes.

7. The apparatus of claim 6 wherein said reading means comprises a constant current source for supplying said deplating current, a counter for indicating the expected remaining life, and a threshold detector responsive to voltage across said cell for stopping said counter when said cell is completely deplated.

8. The apparatus of claim 5 including means for indicating incipient failure of said tube when said integrated failure mode output exceeds a predetermined value, said means for indicating said incipient failure comprising means for detecting complete deplatement of said first electrode, and said predetermined value being represented by the quantity of initial plating on said first electrode.

9. The apparatus of claim 1 wherein said means for monitoring said failure inducive operating condition comprises means for sensing a plurality of operating conditions, and means for deriving outputs indicative of the values of said operating conditions, and wherein said means for deriving an output signal indicative of the value of said failure inducive operating condition comprises means for combining a plurality of said outputs.

10. An apparatus for predicting the failure of an X-ray generator tube, comprising:

means for deriving output signals indicative of the values of the voltage and current of the electrons striking the target of said tube, means for combining said voltage and current signals to derive a signal indicative of the power delivered to said target, means for simulating the heat storage in said target by integrating said power signal in an electric circuit simulating the heat storage and cooling rate of said target, means for deriving a failure mode signal when a selected combination of at least two of the signals indicative of said power, the time application of said power, and said heat storage surpasses a predetermined value, means for integrating successive failure mode signals, and means for indicating a value of said integrated failure mode signals.

11. The apparatus of claim 10 wherein said value of said integrated failure mode outputs is a value determinative of incipient failure.

12. The apparatus of claim 10 further including a plurality of failure mode channels, each channel connected to a separate integrating means, and means for generating a failure mode signal in a selected channel when a selected combination of power, time and heat storage exceeds a value predetermined for said selected channel.

13. The apparatus of claim 10 wherein said selected combination is said duration time during which the product of said power and a predetermined function of said heat storage exceeds a selected reference level, and wherein said predetermined value is a selected time.

14. The apparatus of claim 10 wherein said electric circuit comprises an integrator connected to a parallel combination of a capacitor and a resistive heat dissipation simulation network.

15. The apparatus of claim 14 wherein said heat dissipation simulation network comprises a plurality of parallel branches, each branch including a series connection of a resistor and a gate for gating said resistor into parallel connection with said capacitor, said gates being controlled by the heat storage output of said integrator, whereby the time constant of said electric circuit may be changed as a function of said heat storage to simulate the cooling rate of said target.

16. An apparatus for predicting the failure of an X-ray generator tube, comprising:

means for deriving output signals indicative of the values of the voltage and current of the electrons striking the target of said tube, means for combining said voltage and current signals to derive a signal indicative of the power delivered to said target, means for simulating the heat storage in said target by integrating said power signal in an electric circuit simulating the heat storage and cooling rate of said target, means for deriving an overload signal when said heat storage exceeds a predetermined value, means for integrating successive overload signals, and means for indicating a value of said integrated overload signals.

17. The apparatus of claim 16 wherein said overload signal is a predetermined current value persisting for the time said heat storage exceeds said predetermined value.

18. An apparatus for predicting failure of an X-ray generator tube containing a rotatable target mounted on a bearing inside the vacuum envelope of said tube, said apparatus comprising; means for sensing the vibration of said tube caused by target rotation, means for generating an output signal indicative of said vibration, means for combining said vibration output signal with a reference signal to generate a failure mode output signal, and means for deriving an indication of incipient failure from said failure mode output signal.

19. An apparatus for predicting failure of an X-ray generator tube containing a rotatable target mounted on a bearing inside the vacuum envelope of said tube, said apparatus comprising; means for sensing the vibration of said tube caused by target rotation, means for generating an output signal indicative of said vibration, means for indicating incipient failure when said vibration output exceeds a predetermined value.

20. An apparatus for predicting failure of an X-ray generator tube containing a rotatable target mounted on a bearing inside the vacuum envelope, said apparatus comprising; means for energizing rotation of said target, means for generating an output signal indicative of a predetermined duration after termination of said energizing,
- means for sensing said rotation after termination of said energizing,
- means for generating from said sensing means an output signal indicative of said rotation,
- means for generating a failure mode output when said rotation signal fails to indicate rotation throughout said duration, and
- means responsive to said failure mode output for indicating incipient failure.

21. An apparatus for predicting failure of an X-ray generator tube containing a rotatable target mounted on a bearing inside the vacuum envelope, said apparatus comprising;
- means for monitoring rotation of said target,
- means for generating a rotation output signal indicative of said rotation,
- means for monitoring heat storage in said target,
- means for generating a hot bearing output indicative of said heat storage exceeding a predetermined value,
- means for generating a failure mode output when said rotation output and said hot bearing output are simultaneous, and
- means responsive to said failure mode output for indicating incipient failure.

22. The apparatus of claim 21 wherein said means for indicating incipient failure comprises means for integrating successive failure mode outputs and means for indicating a value of said integrated failure mode outputs.

* * * * *

UNITED STATES PATENT AND TRADEMARK OFFICE
CERTIFICATE OF CORRECTION

PATENT NO. : 3,955,119
DATED : May 4, 1976
INVENTOR(S) : John T. Perry, James A. Grichnik, Joel J. Schmutzer It is certified that error appears in the above-identified patent and that said Letters Patent are hereby corrected as shown below:

Column 7, line 12, change "76" to -- 75 --.

Column 7, line 30, change "91" to -- 81 --.

Column 7, line 46, change "threshold 85" to read -- threshold detector 85 --.

Column 8, line 5, change "gennerator" to -- generator --.

Signed and Sealed this

Twenty-seventh Day of July 1976

[SEAL]

Attest:

RUTH C. MASON
*Attesting Officer*

C. MARSHALL DANN
*Commissioner of Patents and Trademarks*